United States Patent
Wu et al.

(10) Patent No.: US 8,041,584 B2
(45) Date of Patent: Oct. 18, 2011

(54) METHOD AND SYSTEM FOR PATIENT RISK LEVEL EVALUATION

(75) Inventors: Chin-Cheng Wu, Guishan Shiang (TW); Yi-Chen Lu, Taipei (TW); Han-Chao Lee, Taipei (TW); Tong-Ming Hsu, Taipei (TW)

(73) Assignee: Institute for Information Industry, Taipei (TW)

( * ) Notice: Subject to any disclaimer, the term of this patent is extended or adjusted under 35 U.S.C. 154(b) by 299 days.

(21) Appl. No.: 12/327,587

(22) Filed: Dec. 3, 2008

(65) Prior Publication Data

US 2010/0106524 A1    Apr. 29, 2010

(30) Foreign Application Priority Data

Oct. 24, 2008    (TW) ................................ 97140885 A

(51) Int. Cl.
*G06Q 10/00* (2006.01)
*G06Q 50/00* (2006.01)

(52) U.S. Cl. ................................ 705/3; 705/2; 600/300
(58) Field of Classification Search .................. 705/2–3; 600/300
See application file for complete search history.

(56) References Cited

U.S. PATENT DOCUMENTS

| | | | |
|---|---|---|---|
| 2006/0253300 A1* | 11/2006 | Somberg et al. | 705/2 |
| 2008/0120138 A1* | 5/2008 | Morita et al. | 705/3 |
| 2008/0270080 A1* | 10/2008 | Zong | 702/188 |
| 2009/0216556 A1* | 8/2009 | Martin et al. | 705/3 |

OTHER PUBLICATIONS

Glaser, Keeping patients out of the hospital: ProVantage's goal, Feb. 21, 2000, Drug Topics, p. 66.*

* cited by examiner

*Primary Examiner* — Luke Gilligan
(74) *Attorney, Agent, or Firm* — Birch, Stewart, Kolasch & Birch, LLP

(57) ABSTRACT

A method for patient risk level evaluation is provided, implemented with a remote medical care center. The remote medical care center connects with a plurality of health care locations at various locations over a network. Patient data of a plurality of patients is received from the plurality of health care locations via the network. An occurred event for each patient is determined, and each of the occurred events is classified into deteriorating or ameliorating category. The patients corresponding to the same events are sorted into a group, and the patients within the group are ranked according to severity of illness of each patient. A risk score for each patient is determined according to the corresponding event. Patient ranking orders corresponding to the events of the deteriorating and the ameliorating category are generated and displayed.

21 Claims, 5 Drawing Sheets

| patient | deteriorating category | risk score | hospital |
|---|---|---|---|
| 丙 | Septic shock event | 1.23 | H-1 |
| 丁 | Septic event | 0.92 | H-1 |
| 乙 | Septic event | 0.85 | H-2 |
| 甲 | Septic event | 0.83 | H-2 |

| patient | ameliorating category | risk score | hospital |
|---|---|---|---|
| A | weaning event | 0.1 | H-1 |
| B | weaning event | 0.145 | H-1 |

FIG. 4

METHOD AND SYSTEM FOR PATIENT RISK LEVEL EVALUATION

CROSS REFERENCE TO RELATED APPLICATIONS

This application claims priority of Taiwan Patent Application Ser. No. 97140885, filed Oct. 24, 2008. The contents of the Patent application are hereby incorporated by reference.

BACKGROUND

The invention relates to data processing, and in particular to systems and methods for patient risk level evaluation in a remote medical care system.

This section is intended to introduce the reader to various aspects of art, which may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

Demand for remote medical care has recently increased. A remote medical care center communicates with a plurality of health care locations over a network. A physician of the remote medical care center takes care of patients hospitalized in the health care locations.

An inefficient imbalance exists between the number of physicians in the remote medical care center and the number of patients hospitalized in the networked health care locations. It is, therefore, difficult for the physicians in the remote medical care center to provide sufficient care to all of the patients.

In a conventional remote medical care system, caregivers of the networked health care locations provide preliminary assessments of the conditions of patients hospitalized in the corresponding health care location. A designation highlight is labeled within the remote medical care system for each patient to indicate severity of illness thereof. For example: a patient labeled with a red highlight is assessed as having high severity and requiring intensive care from the medical care center; a patient labeled with a yellow highlight is assessed as having middle severity; and a patient labeled with a green highlight is assessed as having low severity. Patients assessed with a high severity have a higher priority for receiving attention from physicians of the medical care center, and patients assessed with a low severity mot often, rarely receive attention from the physicians of the medical care center.

According to the conventional method, patient conditions are determined by caregivers of individual networked health care locations. Meanwhile, criteria used in determining patient conditions are different for different networked health care locations. Thus, within the remote medical care system, there is no standardized practice in determining conditions of patients. Further, for patients with low severity, caregivers of networked health care location don't inform the remote medical care center of their conditions. In addition, because of the limited number of physicians of the remote medical care center, patients assessed as having a low severity, most often, do not receive attention from the physicians of the remote medical care center.

Hence, there is a need for a method and system for providing remote medical care that can effectively assess conditions of patients hospitalized in networked health care locations with uniformed criteria, thus enabling physicians of the remote medical care center to provide overall medical care to all patients, regardless of the severity of their conditions.

SUMMARY

Certain aspects commensurate in scope with the claimed invention are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

A system for patient risk level evaluation is provided. The system is implemented with a remote medical care center, wherein the remote medical care center connects with a plurality of health care locations over a network. The system for patient risk level evaluation comprises an input interface, a processor, and an output interface. The processor comprises an event determination unit, a classification unit, a group sorting unit, a risk evaluation unit, and a category ranking unit. The input interface, connecting to each of the plurality of health care locations, receives patient data for a plurality of patients from the plurality of health care locations. The event determination unit determines which event has occurred to each patient according to the corresponding patient data. The classification unit classifies each of the events into a deteriorating category or an ameliorating category. The group sorting unit sorts the patients corresponding to the same events into a group, and ranks the patients within the group according to severity of illness of each patient. The risk evaluation unit determines a risk score for each patient according to the corresponding event. The category ranking unit generates a patient ranking order, corresponding to the event of the deteriorating category, in the order of a high risk score to a low risk score and generates a patient ranking order, corresponding to the event of the ameliorating category, in the order of a low risk score to a high risk score. The output interface displays the patient ranking order corresponding to the event of the deteriorating category, and displays the patient ranking order corresponding to the event of the ameliorating category.

Also provided is a method for patient risk level evaluation. The method is implemented with a remote medical care center, wherein the remote medical care center connects with a plurality of health care locations over a network. Patient data of a plurality of patients is received, via the network, from the plurality of health care locations. An occurred event for each patient is determined according to the corresponding patient data. Each of the occurred events is classified into a deteriorating category or an ameliorating category. The patients corresponding to the same events are sorted into a group, and the patients within the group are ranked according to severity of illness of each patient. A risk score for each patient is determined according to the corresponding event. A patient ranking order, corresponding to the event of the deteriorating category is generated in the order of a high risk score to a low risk score. A patient ranking order, corresponding to the event of the ameliorating category is generated in the order of a low risk score to a high risk score. The patient ranking order corresponding to the event of the deteriorating category is displayed, and the patient ranking order corresponding to the event of the ameliorating category is displayed.

The method of the present invention, or certain aspects or portions thereof, may take the form of program code embodied in a tangible media.

More specifically, the method of the present invention, or certain aspects or portions thereof, may take the form of program code (i.e. instructions) embodied in a tangible media, such as floppy diskettes, CD-ROMS, hard drives, or any other machine-readable storage medium, wherein, when the program code is loaded into and executed by a machine, such as a computer, the machine becomes an apparatus for practicing the invention. The methods and apparatus of the present invention may also be embodied in the form of program code transmitted over some transmission medium, such as electrical wiring or cabling, through fiber optics, or via any other form of transmission, wherein, when the program code is received and loaded into and executed by a machine, such as a computer, the machine becomes an apparatus for practicing the invention. When implemented on a general-purpose processor, the program code combines with the processor to provide a unique apparatus that operates analogously to specific logic circuits.

BRIEF DESCRIPTION OF DRAWINGS

The invention can be more fully understood by reading the subsequent detailed description and examples with references made to the accompanying drawings, wherein:

FIG. 4 illustrates an embodiment of a screen display presenting a ranking order of patients.

DETAILED DESCRIPTION

One or more specific embodiments of the invention are described below. In an effort to provide a concise description of these embodiments, not all features of an actual implementation are described in the specification. It should be appreciated that in the development of any such actual implementation, as in any engineering or design project, numerous implementation-specific decisions must be made to achieve specific developer goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill in the art having the benefit of this disclosure.

In the following detailed description, reference is made to the accompanying drawings which form a part hereof, shown by way of illustration of specific embodiments. These embodiments are described in sufficient detail to enable those skilled in the art to practice the invention, and it is to be understood that other embodiments may be utilized and that structural, logical and electrical changes may be made without departing from the spirit and scope of the invention. The following detailed description is, therefore, not to be taken in a limiting sense. The leading digit(s) of reference numbers appearing in the figures corresponds to the figure number, with the exception that the same reference number is used throughout to refer to an identical component which appears in multiple figures. It should be understood that the many of the elements described and illustrated throughout the specification are functional in nature and may be embodied in one or more physical entities or may take other forms beyond those described or depicted.

Figure 1:
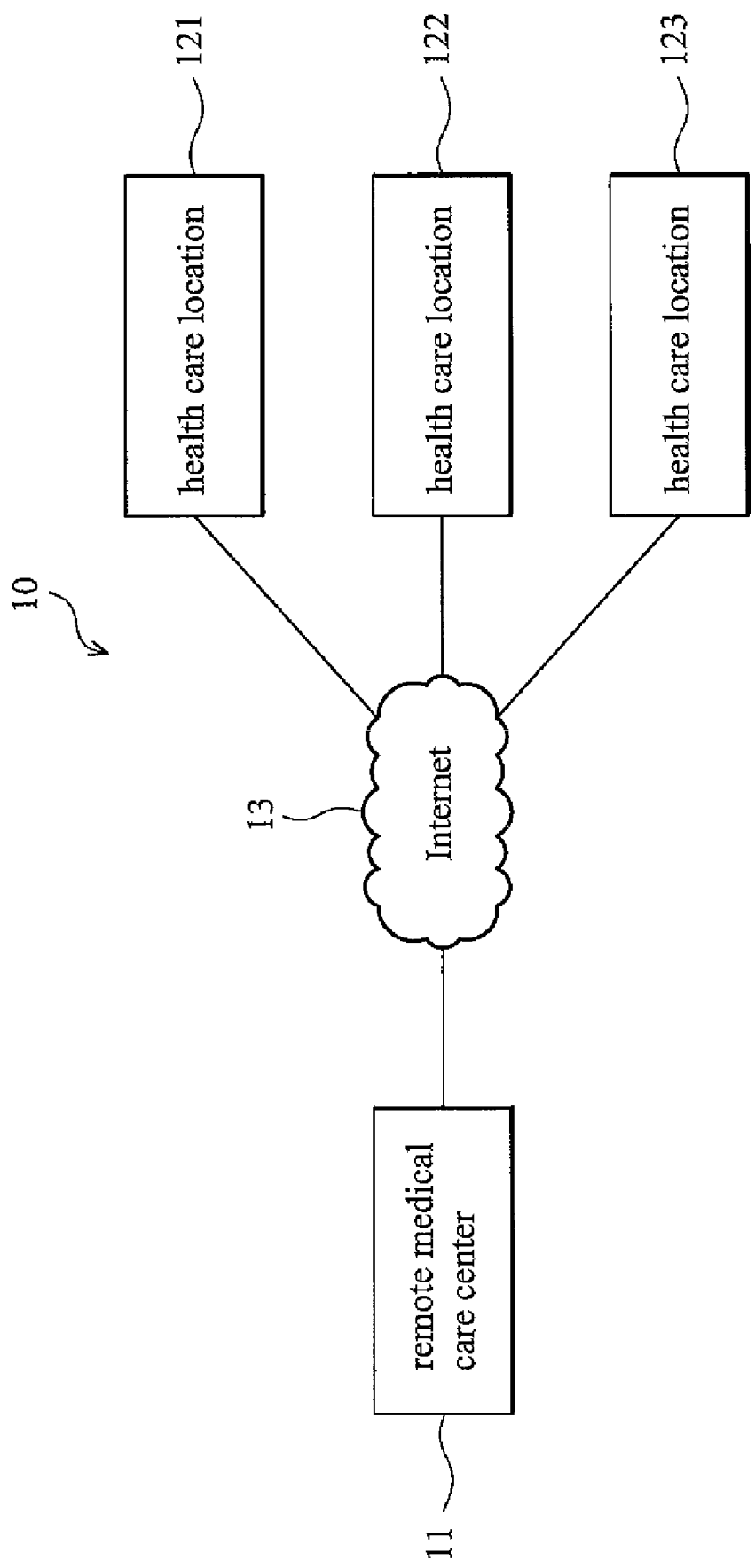
FIG. 1 illustrates an embodiment of a medical care system.

FIG. 1 illustrates an embodiment of a medical care system. The medical care system 10 comprises a remote medical care center 11 and health care locations 121-123. The health care locations can be a clinic, sanatorium, or other organization providing medical services. The number of health care locations is not limited to 3. The remote medical care center 11 connects with health care locations 121~123 over a network 13.

A described system for patient risk level evaluation provided can be implemented with the remote medical care center 11. The system for patient risk level evaluation is capable of effective and standardized evaluation of conditions of patients at various health care locations, and overall medical care to all patients, regardless of the severity of their conditions.

Figure 2:
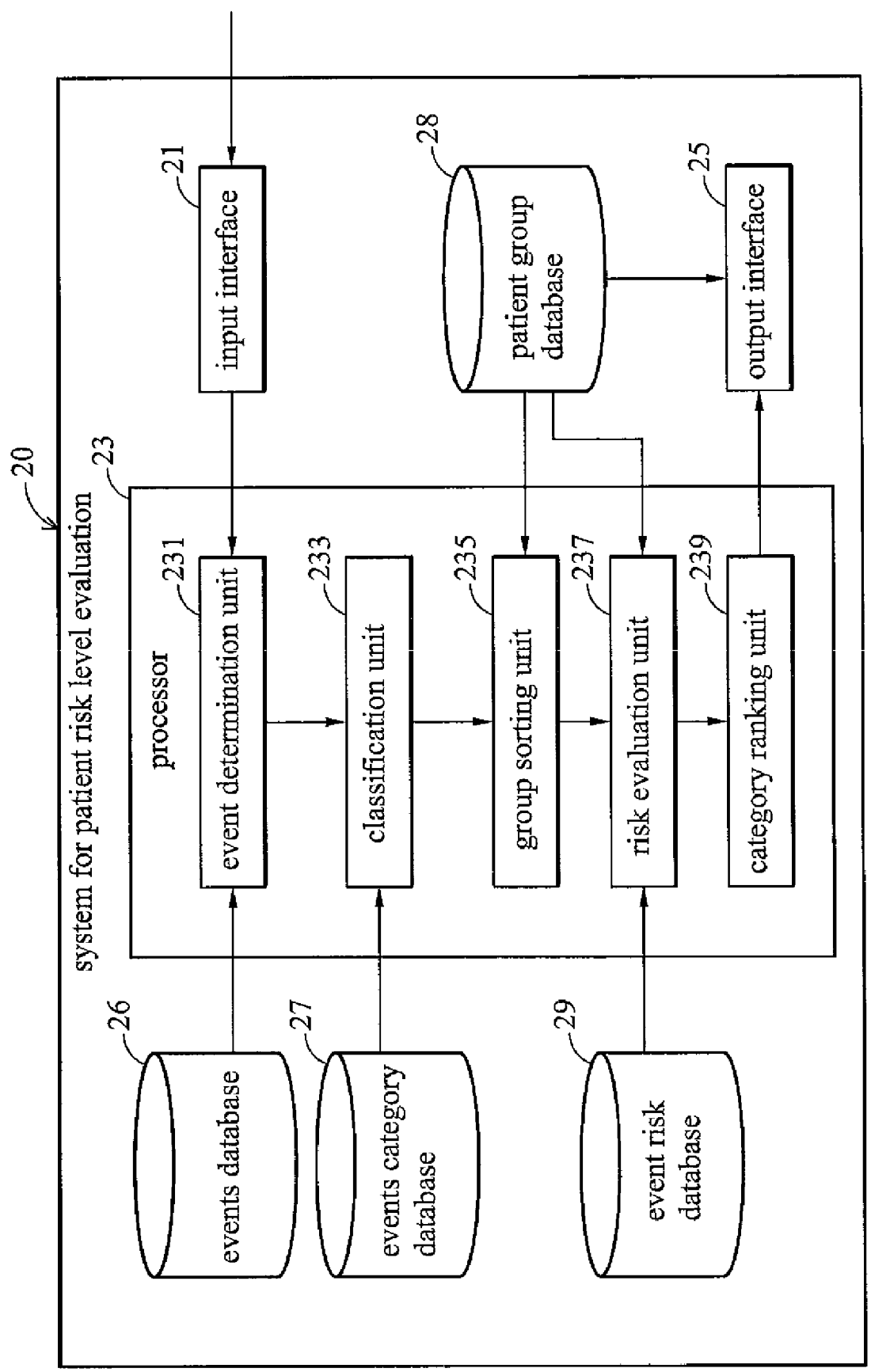
FIG. 2 is an embodiment of a system for patient risk level evaluation.

FIG. 2 is an embodiment of a system for patient risk level evaluation. The system for patient risk level evaluation 20 can be implemented in any electronic device capable of computing, such as a personal computer. The system for patient risk level evaluation 20 can be implemented with a remote medical care center, wherein the remote medical care center connects with a plurality of health care locations at various locations over a network.

The system for patient risk level evaluation 20 comprises an input interface 21, a processor 23, an output interface 25, an events database 26, an events category database 27, a patient group database 28, and an event risk database 29. The processor 23 comprises an event determination unit 231, a classification unit 233, a group sorting unit 235, a risk evaluation unit 237, and a category ranking unit 239.

The input interface 21 connects to each of the plurality of health care locations, and receives patient data for a plurality of patients from the plurality of health care locations. The patient data can comprise data such as basic patient data, historical data, vital sign data, condition evaluation data, laboratory reports, and ventilator settings.

The processor 23 receives the patient data, and determines a risk level for each patient according to the patient data, thus facilitating provision of medical care from the remote medical care center to the health care locations connected with the remote medical care center.

The processor 23 comprises an event determination unit 231, a classification unit 233, a group sorting unit 235, a risk evaluation unit 237, and a category ranking unit 239.

The event determination unit 231 determines which event has occurred to each patient according to the corresponding patient data.

The classification unit 233 classifies each of the events into a deteriorating category or an ameliorating category. For example, events such as a sepsis event and a septic shock event can be put into the deteriorating category; and events such as a weaning event can be put into the ameliorating category.

The group sorting unit 235 sorts the patients corresponding to the same events into a group, and ranks the patients within the group according to severity of illness of each patient.

The risk evaluation unit 237 determines a risk score for each patient according to the corresponding event.

The category ranking unit 239 generates a patient ranking order, corresponding to the event of the deteriorating category in the order of a high risk score to a low risk score, wherein the patient with the highest risk score is placed on the top of the patient ranking order corresponding to the event of the deteriorating category; and generates a patient ranking order, corresponding to the event of the ameliorating category in the order of a low risk score to a high risk score, wherein the patient with the lowest risk score is placed on the top of the patient ranking order corresponding to the event of the ameliorating category.

The output interface 25 can comprise a monitor to display the patient ranking order corresponding to the event of the deteriorating category, and display the patient ranking order corresponding to the event of the ameliorating category. The output interface 25 can issue warning signals pertaining to patients which rise in patient ranking order corresponding to the event of the deteriorating category, and can issue warning signals pertaining to patients which rise in patient ranking order corresponding to the event of the ameliorating category. For example, the output interface 25 can highlight an item corresponding to patients which rise in rank with a light signal.

The event database 26 stores event criteria for each of the events, wherein the event determination unit 231 determines the occurrence of an event for each patient according to the corresponding patient data and the event criteria stored in the event database 26.

The events category database 27 stores the event classified into the deteriorating category and the event classified into the ameliorating category, respectively. The classification unit 233 classifies each of the events into the deteriorating category or the ameliorating category according to the data stored in the events category database 27.

The patient group database 28 stores the patient data according to the group sorted by the group sorting unit 235.

The event risk database 29 stores at least one of the following: mortality risk of each of the events; relative factors of each of the events; weights assigned to each of the relative factors of each of the events; and criterion for determining abnormality level of each of the relative factors.

the risk evaluation unit 237 determines the risk score for each patient based on the corresponding event according to the following equation:

$$A=D+(\Sigma W_i E_i).$$

wherein 'A' is the risk score of the corresponding patient, 'D' is a mortality risk of the occurred event of the corresponding patient, 'W' is a weight of the relative factors of the occurred event of the corresponding patient, and 'E' is a score reflecting the abnormality level of the relative factors of the occurred event of the corresponding patient.

Figure 3A:
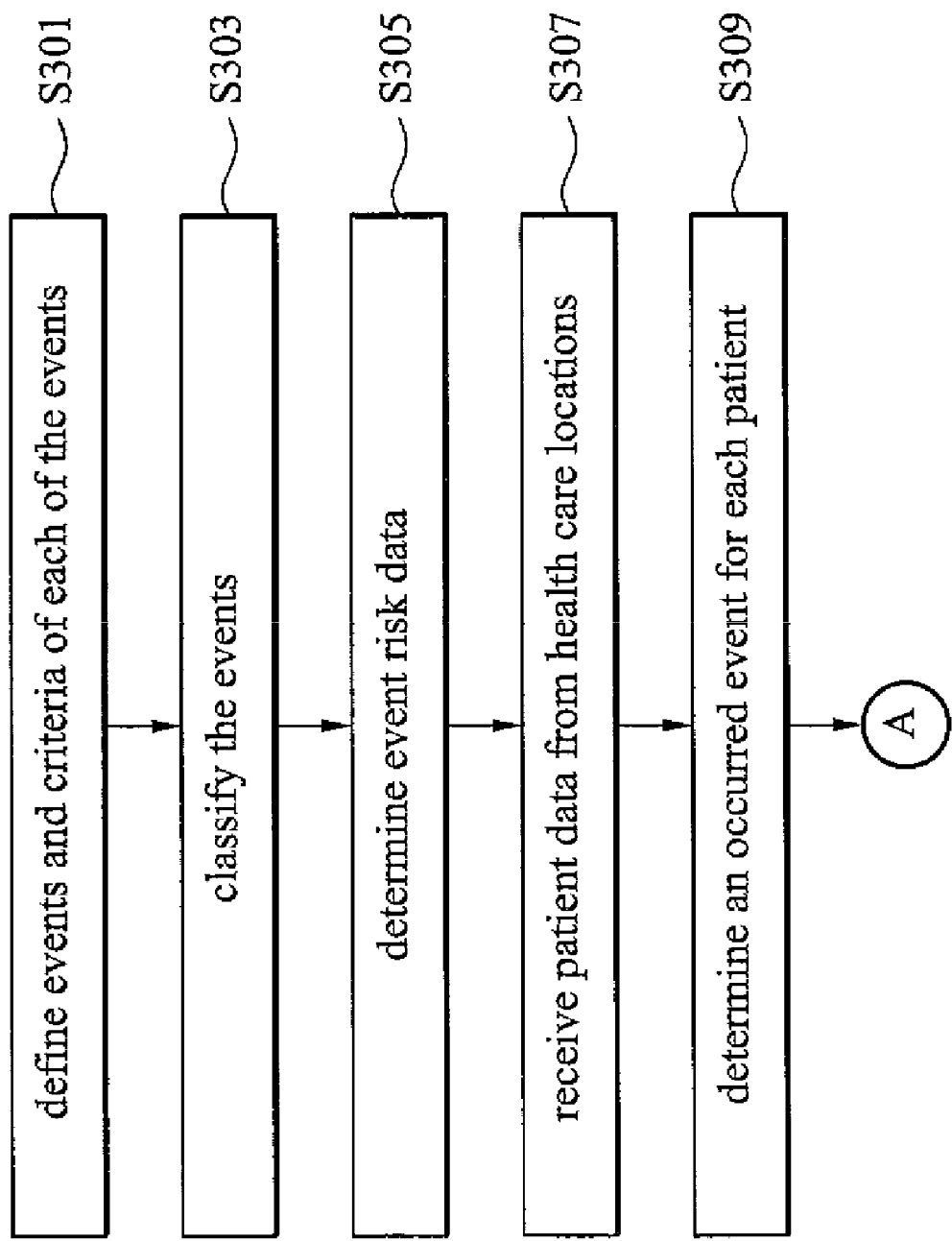
FIG. 3 is flowchart of an embodiment of a method for patient risk level evaluation.
Figure 3B:
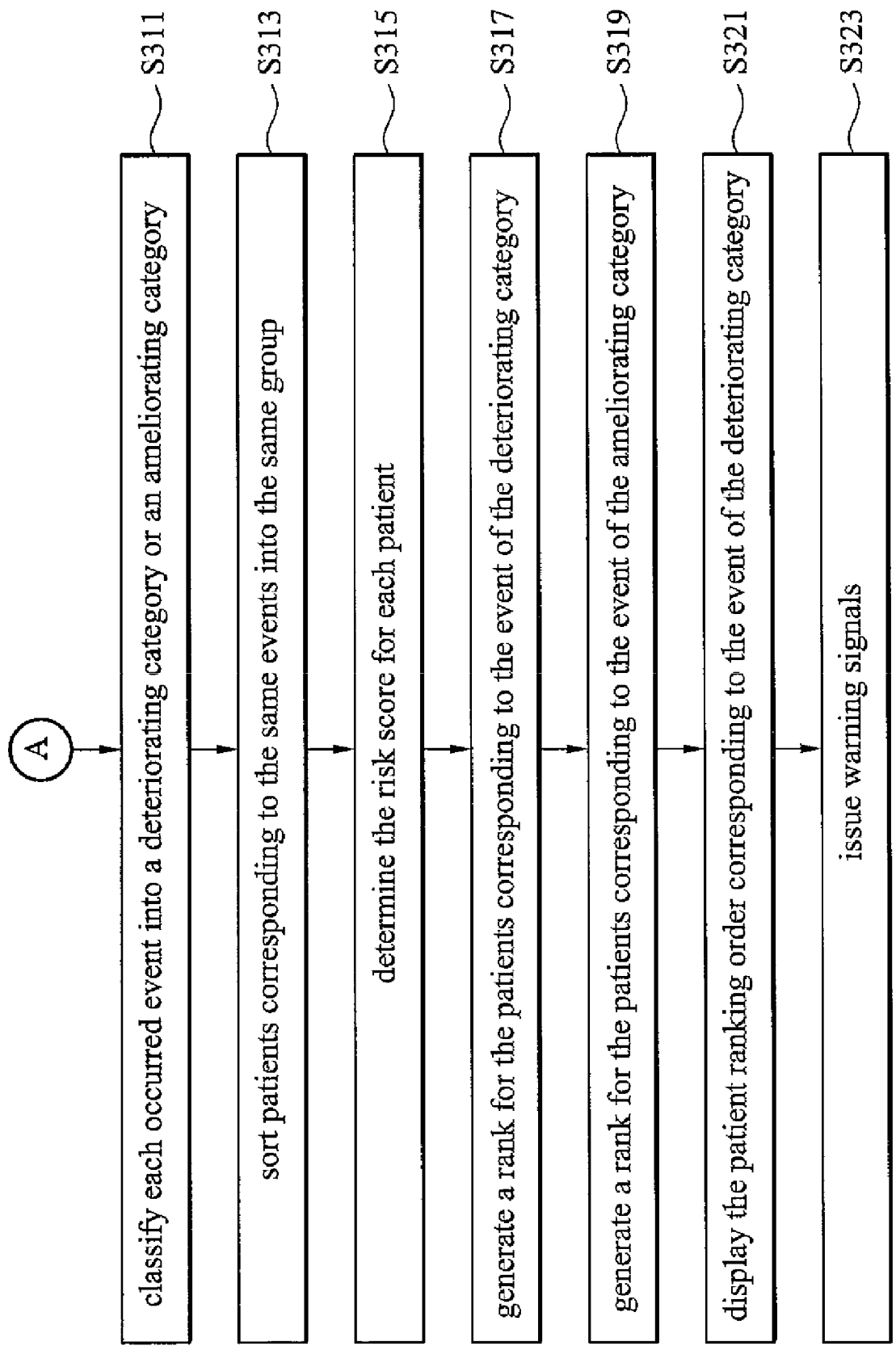

FIGS. 3A and 3B are flowcharts of an embodiment of a method for patient risk level evaluation. The method for patient risk level evaluation is implemented with a remote medical care center, wherein the remote medical care center connects with a plurality of health care locations over a network. The method for patient risk level evaluation can be implemented in the systems illustrated in FIG. 1 and FIG. 2.

Pertinent data is required for implementing this method.

In step S301, events are defined and criteria of each of the events are provided.

In step S303, the events are classified. For example, an event is put into a deteriorating category or an ameliorating category.

In step S305, event risk data is determined. The event risk data can comprise at least one of the following: mortality risk of each of the events; relative factors of each of the events; weights assigned to each of the relative factors of each of the events; and criterion for determining abnormality level of each of the relative factors.

According to the method, patient data of a plurality of patients is received, via a network, from the plurality of health care locations (step S307). The patient data comprises at least one of the following: basic patient data; historical data; vital sign data; condition evaluation data; laboratory reports; and ventilator settings.

In step S309, an occurred event for each patient is determined according to the corresponding patient data and the criterion of each of the events.

In step S311, each of the occurred events is classified into a deteriorating category or an ameliorating category according to the settings determined in step S303.

In step S313, the patients corresponding to the same events are sorted into the same group, and results of the sorting are stored in a patient group database.

In step S315, the risk score for each patient is determined based on the corresponding event risk data set in step S305. The risk score is calculated according to the following equation:

$$A=D+(\Sigma W_i E_i),$$

wherein 'A' is the risk score of the corresponding patient, 'D' is a mortality risk of the occurred event for the corresponding patient, 'W' is a weight of the relative factors of the occurred event for the corresponding patient, and 'E' is a score reflecting the abnormality level of the relative factors of the occurred event for the corresponding patient.

In addition, the patients within the group can be ranked according to severity of illness (reflected by the risk score) of each patient.

In step S317, a rank is generated for the patients corresponding to the event of the deteriorating category in the order of a high risk score to a low risk score.

In step S319, a rank is generated for the patients corresponding to the event of the ameliorating category in the order of a low risk score to a high risk score.

In step S321, the patient ranking order corresponding to the event of the deteriorating category is displayed, and the patient ranking order corresponding to the event of the ameliorating category is displayed.

In step S323, warning signals are issued, wherein the warning signals pertain to patients who rise in patient ranking order corresponding to the event of the deteriorating category, and warning signals are issued, wherein the warning signals pertain to patients who rise in patient ranking order corresponding to the event of the ameliorating category. For example, the warning signals can be presented by light signals.

Here, an exemplary embodiment is provided.

First, several events are defined and criterion of each of the events is provided in advance. The events are next classified. In addition, event risk data is provided for each of the events. Here, the described data is provided and defined according to statistical clinic data.

In this embodiment, three events are referred to as examples.

(1) Sepsis Event:

Criteria of a Sepsis Event:

Any two of the following conditions occur in a particular batch of vital sign data: body temperature higher than 38.5 degrees centigrade; pulse rate higher than 100 pulses/minute; respiratory rate higher than 25 times/minute; number of white blood cells higher than 12000.

Category:

deteriorating category

Event Risk Data:

1. mortality risk: 50%;
2. relative factors: respiratory rate, number of white blood cells, pulse rate, and body temperature;
3. weights assigned to each of the relative factors: weight of respiratory rate is 0.4; weight of number of white blood cells is 0.3; weight of pulse rate is 0.2; and weight of body temperature is 0.1; and
4. criterion for determining abnormality level of each of the relative factors, wherein, abnormality levels are indicated by light signal grades, such as a red light grade, a yellow light grade, and a green light grade. Criteria for each grade are determined by experts. For example, a relative factor indicated by a red light grade is assigned an abnormality score of 0.7, a relative factor indicated by a yellow light grade is assigned an abnormality score of 0.3 and a relative factor indicated by a green light grade is assigned an abnormality score of 0.

(2) Septic Shock Event:
Criteria of a Septic Shock Event:
If systolic pressure rises above 90 mmHg within three days after a sepsis event has occurred, then it is determined that a septic shock event has occurred.
Category:
deteriorating category
Event Risk Data:
1. mortality risk: 80%;
2. relative factors: blood pressure, respiratory rate, pulse rate, body temperature, and number of white blood cells;
3. weights assigned to each of the relative factors: weight of blood pressure is 0.4; weight of respiratory rate is 0.2; weight of pulse rate is 0.2; weight of body temperature is 0.1; and weight of number of white blood cells is 0.1;
4. criterion for determining abnormality level of each of the relative factors, wherein abnormality levels are indicated by light signal grades, such as a red light grade, a yellow light grade, and a green light grade. Criteria for each grade are determined by experts. For example, a relative factor indicated by a red light grade is assigned an abnormality score of 0.7, a relative factor indicated by a yellow light grade is assigned an abnormality score of 0.3, and a relative factor indicated by a green light grade is assigned an abnormality score of 0.

(3) Weaning Event:
Criteria of a Weaning Event:
All of the following conditions occur in a particular batch of vital sign data: systolic pressure lower than 90 mmHg; pulse rate higher than 50 pulses/minutes and lower than 130 pulses/minute; body temperature lower than 38 degrees centigrade; $FiO_2$ lower than 50%; Positive End Expiratory Pressure (PEEP) lower than 8 $cmH_2O$; respiratory rate lower than 35 times/minute; tidal volume (TV) higher than 300 ml; and $SpO_2$ higher than 90%.
Category:
ameliorating category
Event Risk Data:
1. mortality risk: 10%;
2. relative factors: $SpO_2$, tidal volume (TV), respiratory rate, Positive End Expiratory Pressure (PEEP), $FiO_2$, pulse rater systolic pressure, and body temperature;
3. weights assigned to each of the relative factors: weight of $SpO_2$ is 0.2; weight of tidal volume (TV) is 0.2; weight of respiratory rate is 0.15; weight of Positive End Expiratory Pressure (PEEP) is 0.15; weight of $FiO_2$ is 0.1; weight of pulse rate is 0.1; weight of systolic pressure is 0.05; and weight of body temperature is 0.05;
4. criterion for determining abnormality level of each of the relative factors, wherein abnormality levels are presented by light signal grades, such as a red light grade, a yellow light grade, and a green light grade. Here, the weaning event is classified as ameliorating category. Relative factors of the weaning event are indicated by a green light and are assigned an abnormality score of 0.

The remote medical center links to the health care locations over a network, and receives, periodically (for example, with a one day period), patient data of a plurality of patients from the plurality of health care locations. The patient data comprises at least one of the following: basic patient data, historical data, vital sign data, condition evaluation data, laboratory reports, ventilator settings.

Table 1 and Table 2 illustrate exemplary vital sign data of an embodiment of patient data.

Table 1 illustrates vital sign data of patient M, patient N, patient O, and patient P.

TABLE 1

| patient | time | body temperature | pulse rate | respiratory rate | systolic pressure | diastolic pressure | white blood cells |
|---|---|---|---|---|---|---|---|
| M | Apr. 3, 2008 23:00 | 38.6 | 123 | 23 | 144 | 56 | 9800 |
| N | Apr. 3, 2008 23:00 | 39.6 | 88 | 30 | 136 | 65 | 10000 |
| O | Apr. 3, 2008 23:00 | 37.6 | 90 | 26 | 85 | 62 | 10000 |
|   | Apr. 2, 2008 23:00 | 37.6 | 90 | 27 | 110 | 62 | 13000 |
| P | Apr. 3, 2008 23:00 | 38.3 | 118 | 23 | 114 | 70 | 14000 |

Table 2 illustrates vital sign data of ventilator patient A, ventilator patient B, ventilator patient C.

TABLE 2

| patient | systolic pressure | pulse rate | body temperature | FiO2 | PEEP | respiratory rate | TV | SPO2 |
|---|---|---|---|---|---|---|---|---|
| A | 120 | 87 | 37.4 | 34 | 5 | 22 | 400 | 98 |
| B | 128 | 76 | 36.8 | 45 | 5 | 23 | 350 | 95 |
| C | 104 | 100 | 38.2 | 52 | 5 | 28 | 320 | 88 |

An occurred event for each patient is determined according to the corresponding patient data.

Here, it is determined that a sepsis event has occurred to patients M, N, and P, a septic shock event has occurred to patient O, and a weaning event has occurred to ventilator patients A and B. In addition, it is determined that a weaning event has not yet occurred to ventilator patient C.

Note that it is determined whether the event of the particular patient is a deteriorating category or an ameliorating category according to the predetermined settings.

The patients corresponding to the same events are sorted into a group. Here, patients M, N, and P correspond to a sepsis event. Accordingly, patients M, N, and P are sorted into a sepsis event group. In addition, patient O is the only member of a septic shock event group, and patients A and B are sorted into a weaning event group.

A risk score for each patient is determined based on the corresponding event and the preset event risk data according to the following equation:

$$A = D + (\Sigma W_i E_i),$$

wherein 'A' is the risk score of the corresponding patient, 'D' is a mortality risk of the occurred event for the corresponding patient, 'W' is a weight of the relative factors of the occurred event for the corresponding patient, and 'E' is a score reflecting the abnormality level of the relative factors of the occurred event for the corresponding patient.

Table 3-1~3-6 illustrate risk scores of patients M, N, O, P and patients A, B, and C.

TABLE 3-1 risk score of patient M

| relative factor | weight | abnormality level | risk score of relative factor |
|---|---|---|---|
| respiratory rate | 0.4 | yellow light 0.3 | 0.12 |
| number of white blood cells | 0.3 | green light 0 | 0 |
| pulse rate | 0.2 | red light 0.7 | 0.14 |
| body temperature | 0.1 | red light 0.7 | 0.07 |
| sum | | | 0.33 |
| mortality risk of sepsis event | | | 0.5 |
| total | | | 0.83 |

TABLE 3-2 risk score of patient N

| relative factor | weight | abnormality level | risk score of relative factor |
|---|---|---|---|
| respiratory rate | 0.4 | red light 0.7 | 0.28 |
| number of white blood cells | 0.3 | green light 0 | 0 |
| pulse rate | 0.2 | green light 0 | 0 |
| body temperature | 0.1 | red light 0.7 | 0.07 |
| sum | | | 0.35 |
| mortality risk of sepsis event | | | 0.5 |
| total | | | 0.85 |

TABLE 3-3 risk score of patient O

| relative factor | weight | abnormality level | risk score of relative factor |
|---|---|---|---|
| blood pressure | 0.4 | red light 0.7 | 0.28 |
| respiratory rate | 0.2 | red light 0.7 | 0.14 |
| pulse rate | 0.2 | yellow light 0.3 | 0.06 |
| body temperature | 0.1 | green light 0 | 0 |
| number of white blood cells | 0.1 | green light 0 | 0 |
| sum | | | 0.48 |
| mortality risk of sepsis event | | | 0.8 |
| total | | | 1.28 |

TABLE 3-4 risk score of patient P

| relative factor | weight | abnormality level | risk score of relative factor |
|---|---|---|---|
| respiratory rate | 0.4 | green light 0 | 0 |
| number of white blood cells | 0.3 | red light 0.7 | 0.21 |
| pulse rate | 0.2 | red light 0.7 | 0.14 |
| body temperature | 0.1 | red light 0.7 | 0.07 |
| sum | | | 0.42 |
| mortality risk of sepsis event | | | 0.5 |
| total | | | 0.92 |

TABLE 3-5 risk score of patient A

| relative factor | weight | abnormality level | risk score of relative factor |
|---|---|---|---|
| SpO$_2$ | 0.2 | green light 0 | 0 |
| TV | 0.2 | green light 0 | 0 |
| respiratory rate | 0.15 | green light 0 | 0 |
| PEEP | 0.15 | green light 0 | 0 |
| FiO$_2$ | 0.1 | green light 0 | 0 |
| pulse rate | 0.1 | green light 0 | 0 |
| systolic pressure | 0.05 | green light 0 | 0 |
| body temperature | 0.05 | green light 0 | 0 |
| sum | | | 0 |
| mortality risk of sepsis event | | | 0.1 |
| total | | | 0.1 |

TABLE 3-6 risk score of patient B

| relative factor | weight | abnormality level | risk score of relative factor |
|---|---|---|---|
| SpO$_2$ | 0.2 | green light 0 | 0 |
| TV | 0.2 | green light 0 | 0 |
| respiratory rate | 0.15 | green light 0 | 0 |
| PEEP | 0.15 | green light 0 | 0 |
| FiO$_2$ | 0.1 | green light 0 | 0 |
| pulse rate | 0.1 | yellow light 0.3 | 0.03 |
| systolic pressure | 0.05 | green light 0 | 0 |
| body temperature | 0.05 | yellow light 0.3 | 0.015 |
| sum | | | 0.045 |
| mortality risk of sepsis event | | | 0.1 |
| total | | | 0.145 |

A rank is generated for the patients corresponding to the event of the deteriorating category in the order of a high risk score to a low risk score. Here, patients M, N, O, and P correspond to the event of the deteriorating category, the rank is O-P-N-M.

A rank is generated for the patients corresponding to the event of the ameliorating category in the order of a low risk score to a high risk score. Here, patients A and B correspond to the event of the ameliorating category, the rank is A-B.

The patient ranking order corresponding to the event of the deteriorating category is displayed, and the patient ranking order corresponding to the event of the ameliorating category is displayed.

FIG. 4 illustrates an embodiment of a screen display presenting a ranking order of patients.

The screen display 40 comprises ranking 41 for a deteriorating category and ranking 45 for an ameliorating category.

In the screen display 40, warning signals can be presented, wherein the warning signals pertain to patients who rise in patient ranking order corresponding to the event of the deteriorating category, and pertains to patients who rise in patient ranking order corresponding to the event of the ameliorating category.

While the invention has been described by way of example and in terms of preferred embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A system for patient risk level evaluation, implemented with a remote medical care center, wherein the remote medical care center connects with a plurality of health care locations over a network, comprising:
   an input interface, connecting to each of the plurality of health care locations, receiving patient data of a plurality of patients from the plurality of health care locations;
   a processor, comprising:
      an event determination unit, determining an occurred event for each patient according to the corresponding patient data;
      a classification unit, classifying each of the occurred events into a deteriorating category or an ameliorating category;
      a group sorting unit, sorting the patients corresponding to the same events into a group, and ranking the patients within the group according to severity of illness of each patient;
      a risk evaluation unit, determining a risk score for each patient based on the corresponding event according to the equation $A=D+(\Sigma W_i E_i)$, wherein A is the risk score of the corresponding patient, D is a mortality risk of the occurred event for the corresponding patient, W is a weight of the relative factors of the occurred event for the corresponding patient, and E is a score reflecting the abnormality level of the relative factors of the occurred event for the corresponding patient; and
      a category ranking unit, generating a patient ranking order for the deteriorating category corresponding to the risk score in the order from high to low, and generating a patient ranking order for the ameliorating category corresponding to the risk score in the order from low to high, respectively; and
   an output interface, displaying the patient ranking order for the deteriorating category, and displaying the patient ranking order for the ameliorating category.

2. The system for patient risk level evaluation of claim 1, wherein the patient data comprises at least one of the following: basic patient data, historical data, vital sign data, condition evaluation data, laboratory reports, ventilator settings.

3. The system for patient risk level evaluation of claim 1, further comprising an events database for storing event criteria for each of the events, wherein the event determination unit determines the occurred event for each patient according to the corresponding patient data and the event criteria.

4. The system for patient risk level evaluation of claim 1, further comprising an events category database for storing the event classified into the deteriorating category and the event classified into the ameliorating category, respectively, wherein the classification unit classifies each of the events into the deteriorating category or the ameliorating category according to the data stored in the events category database.

5. The system for patient risk level evaluation of claim 1, further comprising a patient group database for storing the patient data according to the group sorted by the group sorting unit.

6. The system for patient risk level evaluation of claim 1, further comprising an event risk database for storing at least one of the following: mortality risk of each of the events; relative factors of each of the events; weights assigned to each of the relative factors of each of the events; and criterion for determining abnormality level of each of the relative factors.

7. The system for patient risk level evaluation of claim 1, wherein the output interface further issues warning signals pertaining to patients which rise in patient ranking order for the deteriorating category, and issues warning signals pertaining to patients which rise in patient ranking order for the ameliorating category.

8. A method for patient risk level evaluation, implemented by a system with a remote medical care center, wherein the remote medical care center connects with a plurality of health care locations over a network and the system comprises an input interface, a processor, and an output interface, comprising:
   receiving, by the input interface and via the network, patient data of a plurality of patients from the plurality of health care locations;
   determining an occurred event for each patient by an event determination unit of the processor according to the corresponding patient data;
   classifying each of the occurred events into a deteriorating category or an ameliorating category by a classification unit of the processor;
   sorting the patients by a group sorting unit of the processor corresponding to the same events into a group, and ranking the patients within the group by the group sorting unit of the processor according to severity of illness of each patient;
   determining a risk score for each patient by a risk evaluation unit based on the corresponding event according to the equation $A=D+(\Sigma W_i E_i)$, wherein A is the risk score of the corresponding patient, D is a mortality risk of the occurred event for the corresponding patient, W is a weight of the relative factors of the occurred event for the corresponding patient, and E is a score reflecting the abnormality level of the relative factors of the occurred event for the corresponding patient;
   generating a patient ranking order for the deteriorating category corresponding to the risk score in the order from high to low by a category ranking unit of the processor;
   generating a patient ranking order for the ameliorating category corresponding to the risk score in the order from low to high by the category ranking unit; and
   displaying the patient ranking order for the deteriorating category by the output interface, and displaying the patient ranking order for the ameliorating category by the output interface.

9. The method for patient risk level evaluation of claim 8, wherein the patient data comprises at least one of the following: basic patient data, historical data, vital sign data, condition evaluation data, laboratory reports, and ventilator settings.

10. The method for patient risk level evaluation of claim 8, further comprising providing an events database for storing event criteria for each of the events, wherein the event determination unit determines the occurred event for each patient according to the corresponding patient data and the event criteria.

11. The method for patient risk level evaluation of claim 8, further comprising providing an events category database for storing the event classified into the deteriorating category and the event classified into the ameliorating category, respectively, wherein the classification unit classifies each of the occurred events into the deteriorating category or the ameliorating category according to the data stored in the events category database.

12. The method for patient risk level evaluation of claim 8, further comprising providing a patient group database for storing the patient data according to the group sorted by the group sorting unit.

13. The method for patient risk level evaluation of claim 8, further comprising providing an event risk database for storing at least one of the following: mortality risk of each of the events; relative factors of each of the events; weights assigned to each of the relative factors of each of the events; and criterion for determining abnormality level of each of the relative factors.

14. The method for patient risk level evaluation of claim 8, further issuing warning signals pertaining to patients which rise in patient ranking order for the deteriorating category, and issuing warning signals pertaining to patients which rise in patient ranking order for the ameliorating category.

15. A non-transitory computer readable storage medium for storing a computer program which is loaded into and executed by a machine to perform a method for patient risk level evaluation, the performed method comprising:
   receiving, via the network, patient data of a plurality of patients from the plurality of health care locations;
   determining an occurred event for each patient according to the corresponding patient data;
   classifying each of the occurred events into a deteriorating category or an ameliorating category;
   sorting the patients corresponding to the same events into a group, and ranking the patients within the group according to severity of illness of each patient;
   determining a risk score for each patient based on the corresponding event according to the equation $A = D + (\Sigma W_i E_i)$, wherein A is the risk score of the corresponding patient, D is a mortality risk of the occurred event for the corresponding patient, W is a weight of the relative factors of the occurred event for the corresponding patient, and E is a score reflecting the abnormality level of the relative factors of the occurred event for the corresponding patient;
   ranking the patients for the deteriorating category in the order from high to low;
   ranking the patients for the ameliorating category in the order from low to high; and
   displaying the patient ranking order for the deteriorating category, and displaying the patient ranking order for the ameliorating category.

16. The non-transitory computer readable storage medium of claim 15, wherein the patient data comprises at least one of the following: basic patient data, historical data, vital sign data, condition evaluation data, laboratory reports, ventilator settings.

17. The non-transitory computer readable storage medium of claim 15, further comprising providing an events database for storing event criteria for each of the events, wherein the event determination unit determines the occurred event for each patient according to the corresponding patient data and the event criteria.

18. The non-transitory computer readable storage medium of claim 15, further comprising providing an events category database for storing the event classified into the deteriorating category and the event classified into the ameliorating category, respectively; wherein the classification unit classifying each of the occurred events into the deteriorating category or the ameliorating category according to the data stored in the events category database.

19. The non-transitory computer readable storage medium of claim 15, further comprising providing a patient group database for storing the patient data according to the group sorted by the group sorting unit.

20. The non-transitory computer readable storage medium of claim 15, further comprising providing an event risk database for storing at least one of the following: mortality risk of each of the events; relative factors of each of the events; weights assigned to each of the relative factors of each of the events; and criterion for determining abnormality level of each of the relative factors.

21. The non-transitory computer readable storage medium of claim 15, further issuing warning signals pertaining to patients which rise in patient ranking order for the deteriorating category, and issuing warning signals pertaining to patients which rise in patient ranking order for the ameliorating category.

* * * * *